United States Patent [19]
Taylor et al.

[11] Patent Number: 5,869,104
[45] Date of Patent: Feb. 9, 1999

[54] METHOD FOR TREATING DERMATOLOGICAL CONDITIONS INCLUDING IMPETIGO

[76] Inventors: Lesli A. Taylor; Ralph L. Bass, both of 3708 Sweeten Creek Rd., Chapel Hill, N.C. 27514

[21] Appl. No.: 934,174

[22] Filed: Sep. 19, 1997

[51] Int. Cl.⁶ .................................................. A61K 33/14
[52] U.S. Cl. ......................... 424/680; 514/861; 514/863; 514/865
[58] Field of Search ............................ 424/680; 514/861, 514/863, 865

[56] References Cited

U.S. PATENT DOCUMENTS

| | | | |
|---|---|---|---|
| Re. 29,799 | 10/1978 | Agusti | 424/241 |
| 3,574,854 | 4/1971 | Bossard | 424/357 |
| 3,808,310 | 4/1974 | Andelfinger et al. | 423/472 |
| 3,867,522 | 2/1975 | Kligman | 424/153 |
| 3,899,581 | 8/1975 | Agusti | 424/241 |
| 4,107,161 | 8/1978 | Agusti | 260/239.55 |
| 4,943,432 | 7/1990 | Biener | 424/647 |
| 5,360,811 | 11/1994 | Tegeler et al. | 514/357 |
| 5,550,247 | 8/1996 | Tegeler et al. | 546/314 |
| 5,654,013 | 8/1997 | Taylor et al. | 424/680 |

FOREIGN PATENT DOCUMENTS

96/28971  9/1996  WIPO .

OTHER PUBLICATIONS

Crowley, "Invasion of the Superbugs", *Medical Report*, (Oct. 1995), pp. 58–59.

D. Van Nostrand, "Van Nostrand's Scientific Encyclopedia", (1938), pp. 548–549.

Morton Salt Product Data Sheet, (Mar. 1995).

Morton Salt Data Sheet, (Apr. 1994).

University Erlangen, Department of Dermatology, (Aug. 8, 1997).

*Skin Disease Weekly*, (Jul. 23, 1997).

*Primary Examiner*—Leonard Schenkman
*Attorney, Agent, or Firm*—Jenkins & Wilson, P.A.

[57] ABSTRACT

A method for the topical treatment of skin affected with a dermatological condition selected from the group consisting of impetigo, epidermolysis bullosa, eczema, neurodermatitis, psoriasis, pruritis, erythema, hidradenitis suppurativa, warts, diaper rash, jock itch, and combinations thereof. For most conditions, sodium chloride, in a substantially pure form as a solid block, is topically applied to the affected skin by gently gliding the block over the affected skin in a manner insufficient to cause abrasion and debridement of the affected skin. For certain conditions, such as epidermolysis bullosa, sodium chloride in the form of an aqueous solution preferably should be used. The applied sodium chloride is left on the skin.

8 Claims, No Drawings

METHOD FOR TREATING DERMATOLOGICAL CONDITIONS INCLUDING IMPETIGO

TECHNICAL FIELD

The present invention relates, in general, to a method for the topical treatment of human skin. More particularly, the present invention relates to an improved method for the topical treatment of human skin affected with a dermatological condition selected from the group consisting of impetigo, epidermolysis bullosa, dermatosis, eczema, neurodermatitis, psoriasis, pruritis, erythema, hidradenitis suppurativa, warts, diaper rash, jock itch, and combinations thereof by gently applying sodium chloride on the affected skin.

BACKGROUND OF THE INVENTION

As is well known, skin conditions are typically treated with antibiotics (oral and/or topical). Often, the antibiotic becomes ineffective over time (typically, within about 6 months after initiating use) due to mutations of the microorganisms causing the skin condition.

Of interest, Agusti U.S. Pat. No. 3,899,581, U.S. Pat. No. 4,107,161, and Reissue Pat. No. 29,799 (a Divisional of the patent application that issued as U.S. Pat. No. 4,107,161) show triamcinolone acetonide for the topical treatment of dermatosis, eczema, neurodermatitis, impetigo, psoriasis, pruritis, and erythema. On the other hand, Tegeler et al. U.S. Pat. No. 5,360,811 (Parent) and U.S. Pat. No. 5,550,247 (Divisional) show various 1,3-propanediols substituted with 1-alkyl-, 1-alkynyl-, or 1-alkynylaryl-2-amino- in a topical application to inhibit bacterial and fungal growth.

Also, of interest is a method of treatment of acne-affected skin and/or rosacea-affected skin with a NaCl block disclosed in published PCT International Application WO 96/28971 to Taylor and Bass, published on Sep. 19, 1996, and having a partial priority to U.S. Ser. No. 08/402,896 which issued as U.S. Pat. No. 5,654,013 on Aug. 5, 1997.

In summary, none of the patents shows sodium chloride topically applied for the treatment of the various subject dermatological conditions recited in the above "Technical Field". Thus, it is still desirable to find a method of treating such skin conditions topically, which method does not require oral ingestion and/or topical application of antibiotics.

STATEMENT OF THE INVENTION

Accordingly, the present invention provides a method for the topical treatment of human skin affected with a dermatological condition selected from the group consisting of impetigo, epidermolysis bullosa, dermatosis, eczema, neurodermatitis, psoriasis, pruritis, erythema, hidradenitis suppurativa, warts, diaper rash, jock itch, and combinations thereof. The method comprises topically applying sodium chloride on the affected skin in a manner insufficient to cause abrasion and debridement of the affected skin, and achieving an improvement in the dermatological condition. It is noted that once the sodium chloride is applied, it is not rinsed off but rather is allowed to remain on the affected skin.

In one embodiment, the sodium chloride is a substantially pure solid block of sodium chloride, preferably obtained from vacuum granulated sodium chloride that has been compressed, as further described below. Preferably, when the sodium chloride is a solid block, it should be about 95% to about 100% by weight, and more preferably, about 97% to about 100% by weight, and even more preferably, about 98% to about 100% by weight, sodium chloride. Furthermore, the sodium chloride block should be free of a carrier, and/or free of topical-type antibiotic medicaments.

To enhance the sodium chloride leaving the block and forming a film or coating on the affected skin, prior to applying the block of sodium chloride on the affected skin, the affected skin is preferably pre-moistened with water, such as from a male shaving the face, a female shaving the legs, a male or female bathing, a male or female splashing water on the affected skin, and the like. Then, the coating of sodium chloride becomes wet when applied to the affected skin and is allowed to dry on the affected skin and remain.

In another embodiment, the sodium chloride is in an aqueous solution, preferably at least 5% by weight sodium chloride. The aqueous solution should be free of topical-type antibiotic medicaments.

Accordingly, it is an object of the present invention to provide a treatment for human skin affected with a dermatological condition selected from the group consisting of impetigo, epidermolysis bullosa, dermatosis, eczema, neurodermatitis, psoriasis, pruritis, erythema, hidradenitis suppurative, warts, diaper rash, jock itch, and combinations thereof, whereby the treatment is effective in the long run (over 6 months), in contrast to the ineffectiveness in the long run (over 6 months) that is typical of topical and oral antibiotic treatments.

It is a further object of the present invention that sodium chloride used in the skin treatment is not orally ingested, and thereby the present invention obviates the risk of nausea, dizziness, or hypertension that can result from oral ingestion of too much sodium chloride.

It is a feature of the present invention that the sodium chloride treatment is also useful in the topical treatment of more than one of the subject skin conditions, which is untrue of standard topical and oral antibiotic medications, each of which is usually condition specific.

Some of the objects and features of the invention having been stated above, others will become evident as the description proceeds, when taken in conjunction with the Laboratory Examples as best described below.

DETAILED DESCRIPTION OF THE INVENTION

Because the present invention involves topical treatment, oral ingestion of drugs used in treating any of the subject dermatological conditions is advantageously avoided. Such oral drugs often have side effects, ranging from annoying to dangerous, especially for females.

For instance, the typical treatment method for persons affected with any of the subject dermatological conditions is oral ingestion of antibiotics, and such treatment for females often results in vaginal yeast infections. Furthermore, certain antibiotics, when orally ingested by a female who is already pregnant or soon becomes pregnant, can cause dangerous side effects, such as fetal abnormalities.

Any affected skin area, such as the face, neck, back, arms, legs, buttocks, or chest of a human, may be topically treated with the method of the present invention. The method may be employed for the treatment of, and is useful for any variation of, a dermatological condition selected from the group consisting of impetigo, epidermolysis bullosa, dermatosis, eczema, neurodermatitis, psoriasis, pruritis, erythema, hidradenitis suppurativa, warts, diaper rash, jock itch, and combinations thereof, whether the condition is mild, severe, or somewhere in between. Furthermore, the method works similarly well in the treatment of both males and females who have any of the subject dermatological conditions.

More specifically, the inventive method involves topically applying sodium chloride, the chemical formula of which is NaCl. When NaCl is in the form of a block, it should be a substantially pure block that should be between about 95% and about 100% by weight NaCl with only trace amounts, if any, present of other ingredients, for instance, other mineral salts such as magnesium chloride or calcium chloride.

Such pure NaCl blocks naturally occur as rock salt, also known as the mineral halite. Halite is translucent when pure, but may be white, yellow, red, or blue when trace amounts of other minerals are present.

Also, Morton Salt of Chicago, Ill. makes substantially pure NaCl blocks, which Morton Salt markets under the trademark BUNNY SALT SPOOLS®. Also, U.S. Pat. Nos. 3,526,508, 3,749,579, and 3,808,310, all to Andelfinger et al. describe BUNNY SALT SPOOLS®.

More particularly, as indicated on the Morton Salt Product Data Sheet that Morton Salt provides to its customers, BUNNY SALT SPOOLS® are plain, white, 3-ounce salt spools having a generally cylindrical shape (i.e, a beveled disc with a center pinhole), which Morton Salt manufactures by compressing vacuum granulated salt. The white spools have a minimum purity of 99.0% NaCl, and may contain certain small amounts of iodide and/or of salts of S, Zn, Mn, Fe, Cu, and/or Co. These white spools are particularly useful in the method of the present invention.

Morton Salt markets the white spools (as well as pink spools under the trademark IOFIXT® and red spools under the trademark IOFIXT® T-M®) for use in feeding salt to small animals such as rabbits, mink, guinea pigs, and chinchillas. The red spools could be used in the subject invention, but supposedly they have their color due to the presence of food coloring in them, and thus, the food coloring probably would leave undesirable color spots on the skin of the person using a red spool.

Additionally, for feeding salt to small animals, Morton Salt makes and sells yellow spools, which are yellow due to the presence of about 3% sulfur and which are about 95% to 97% NaCl. They should also work in the method of the present invention.

It is believed that the particle size of the compressed granules that form the spools is the same as the particle size that is indicated on the Morton Salt Product Data Sheet, provided by Morton Salt to its customers for its NaCl product sold under the trademark PUREX®. PUREX® is a granulated NaCl having a mean average crystal size of 430 microns or 360 microns, depending on whether the product is manufactured at Morton Salt's facility in Rittman, Ohio or Silver Springs, N.Y., respectively.

For use in the present invention, the block of NaCl also should be free of any carriers. For instance, typical pharmaceutically acceptable carriers (such as ethanol, glycerol, stearyl alcohol, and glycerylmono-stearate, often used to place a medicament in solution form or emulsion form for application) need not be used for the present invention, and preferably, are not used.

Even more preferably, the block of NaCl also should be free of any other medicaments for the topical treatment of any of the subject dermatological conditions.

Furthermore, the block of NaCl should be of appropriate size to be conveniently held in the hand of the patient (or other person who may apply it to the patient) so that it may be gently glided onto the affected skin. A convenient size may range from a cubic shape of about 0.5 inch on a side to a rectangular parallelapiped shape of about 1 inch×1 inch×2 inches, and of course, other convenient shapes, such as cylinders, may be used.

The NaCl block is topically applied by very gentle gliding motions, such as dabbing motions, circular motions, up and down motions, or zigzag motions, over the affected skin. Care must be taken so that gently gliding the NaCl over the affected skin is in a manner insufficient to cause abrasion and debridement of the affected skin, which typically will result in exacerbation of the dermatological condition.

The gliding should be accomplished in about 60 seconds to about 1 second, and more preferably in about 45 seconds to about 2 seconds. Typically, the gliding will be accomplished in about 30 seconds to about 15 seconds.

After gliding the block of NaCl over the affected skin, the NaCl, that came off the block and is now applied, is left on the skin. Typically, the applied NaCl forms a thin film or coating on the affected skin.

Preferably, prior to gliding the block of NaCl onto the affected skin, water should be employed to pre-moisten the skin in order to enhance a portion of the NaCl in leaving the block and staying applied on the skin. Then, the applied NaCl has been wetted, and is left to dry on the skin. The pre-moistening can be accomplished, such as by a female shaving the legs and then after splashing water on the legs to remove residual shaving cream, not drying the legs. Moreover, one can pre-moisten the affected skin by simply leaving it wet after bathing it, or by simply splashing water on it.

For certain conditions, such as epidermolysis bullosa, the sodium chloride preferably is in an aqueous solution because epidermolysis bullosa manifests itself in such severe blistering of the skin that even very gentle touching with a NaCl block may cause pieces of skin to fall off, and moreover, the blistering typically covers most of the body. Thus, the patient with epidermolysis bullosa may be placed in a bath (i.e., aqueous solution of NaCl), and left to soak in the bath, for instance, for up to ½ hour, or even longer. For certain conditions, such as warts, it may simply be more convenient to soak the affected area, for instance for 1 to 5 minutes, in an aqueous solution of NaCl, rather than gently gliding a NaCl block on the affected area.

The aqueous solution should be at least 5%, more preferably at least 10%, most preferably at least 20%, by weight NaCl, and may be saturated with NaCl. At room temperature, saturation of NaCl in water is about 32.6% by weight NaCl, and at 0° C. is about 35.7% by weight NaCl.

Application of NaCl to the affected skin should be done at least 1 time per day, but may be oftener depending on the severity of the dermatological condition. Hence, application may be as often as 5 or 6 times per day, or even more. Typically, for most persons, application once or twice per day is sufficient.

Application of NaCl should be repeated (daily, twice daily, etc.) for at least 2 weeks on a regular basis, and the dermatological condition will have been alleviated and often eliminated. For severe cases, application on a regular basis should be for at least 2 times per day and for at least 5 weeks to eliminate the skin condition. However, for epidermolysis bullosa (in which skin infections take hold because of a genetic defect), application of NaCl should continue for the rest of the patient's life. Otherwise, the genetic defect will allow the skin infections to take hold again. Even for other skin conditions, after elimination of the respective conditions, application may be once per day to maintain the skin free of the respective condition.

LABORATORY EXAMPLES

Example I (Testing of Males with Solid NaCl)

Three male persons, respectively with hidradenitis suppurativa, impetigo, or eczema, are treated by the inventive method. A block of mineral pure rock salt having 98% to 100% sodium chloride is used. The block is either from S & S Marketing Company, Tempe, Ariz., or from F/T Limited, P.O. Box 756, Millbrae, Calif. 94030-0756, has a size of about 3 inches×1 inch×1 inch, and is sold for use as an underarm deodorant. The product from S & S contains a trace amount of aluminum alum and the product from F/T contains trace amounts of ammonium alum and aluminum alum. The testing of the three male subjects is as follows:

Test Subject No. 1. This person is an adult male Caucasian afflicted with hidradenitis suppurativa. He is topically applying an antibiotic, as well as orally ingesting another antibiotic, to treat the condition.

Once per day, his affected skin is moistened with water. Then, NaCl from the block is applied to the affected areas by very gently gliding the block of sodium chloride in dabbing motions, circular motions, up and down motions, or zigzag motions (the motions being insufficient to cause debridement and abrasion of the affected skin) on the moistened areas for about 15 to about 30 seconds. A thin film of wetted sodium chloride results, and is allowed to remain and to dry. Simultaneously, he discontinues with the topical application of the one antibiotic, but continues with oral ingestion of the other antibiotic. This once daily application of NaCl, while orally ingesting an antibiotic, continues for 3 weeks.

At the end of 3 weeks, he stops the oral ingestion of the antibiotic, and proceeds in the following manner. He topically applies the block of NaCl twice per day for another 2 weeks, once in the morning, and once in the evening. At the end of 5 weeks, the hidradenitis suppurativa is completely eliminated.

He then stops the NaCl treatment for 2 days, and the hidradenitis suppurativa begins to reappear. Thus, he then returns to the NaCl application twice per day. After 1 week, the hidradenitis suppurativa begins to be alleviated. After 2 weeks, his skin is again clear and the hidradenitis suppurativa completely eliminated. He continues with the twice per day application of NaCl and his skin remains clear.

Test Subject No. 2. This person is an adult male Caucasian afflicted with impetigo.

Once per day, he moistens his affected skin with water. Then, he applies NaCl from the block to the affected areas by very gently gliding the block in dabbing motions, circular motions, up and down motions, or zigzag motions (the motions being insufficient to cause debridement and abrasion of the affected skin) on the moistened areas for about 15 to about 30 seconds. A thin film of wetted sodium chloride results. He allows the film to remain and to dry.

This once daily application continues for 2 weeks. At the end of 1 week, the impetigo begins to be alleviated. At the end of 2 weeks, his skin is clear and the impetigo completely eliminated.

Test Subject No. 3. This person is an adult male Caucasian afflicted with eczema.

Once per day, he moistens his affected skin with water. Then, he applies NaCl from the sodium chloride block to the affected areas by very gently gliding the block in dabbing motions, circular motions, up and down motions, or zigzag motions (the motions being insufficient to cause debridement and abrasion of the affected skin) on the moistened areas for about 15 to about 30 seconds. A thin film of wetted sodium chloride results. He allows the film to remain and to dry.

This once daily application continues for 5 weeks. At the end of 2 weeks, the eczema begins to be alleviated. At the end of 5 weeks, and the eczema is substantially eliminated. He stops the application of NaCl and instead begins using a topical antibiotic. A few days later, the eczema returns with the extreme severity prior to his initiation of the NaCl treatment. He returns to the once daily application of NaCl, and his skin is clear again in 5 weeks.

It is noted that for each of the test subjects nos. 1, 2, and 3, within a few minutes of the first NaCl application, a therapeutic effect is observed in that the redness of inflamed areas diminishes and is hardly noticeable.

Example II (Testing of Females with Solid NaCl)

The method of Example I for male test subjects nos. 1, 2, and 3, but instead with female test subjects nos. 1, 2, and 3, is repeated. The same results are respectively obtained.

Example III (Testing with Aqueous NaCl)

Test Subject No. 1. This person was an adult male Caucasian affected with warts on one hand. Once per day, he soaked the hand for 5 minutes in an aqueous solution of 20% by weight NaCl in tap water. This continued for 5 days, and the warts disappeared. He stopped the treatment, and within 1 week, the warts had returned.

Test Subject No. 2. The method is repeated in the same manner of application of 20% by weight NaCl in tap water, as with the above-noted male test subject no. 1 in this Example III, either once per day, twice per day, or more times, depending on the severity of the condition, but instead with a teenaged female person having epidermolysis bullosa-affected skin. She is placed in a NaCl bath, and soaks in the bath for ½ hour. Treatment at least once per day is continued indefinitely and the results are that the severity of the blisters is markedly reduced by about week 5 of the treatment.

Example IV (Testing with BUNNY SALT SPOOLS®)

Fifteen persons are treated by the inventive method, but with a block of salt that is different in certain respects from the block of salt employed in the testing indicated above in Examples I and II. More specifically, for the following tests, the block of salt employed by each test subject is that marketed under the trademark BUNNY SALT SPOOLS® by Morton Salt of Chicago, Ill.

No complications nor yeast infections result from the use of the spools by any of the fifteen test subjects.

In general, the testing of each of the fifteen subjects is conducted as follows:

Once or twice per day, after wetting the affected areas with water, the subject applies NaCl from the spool to the affected areas by very gently gliding the spool in dabbing motions, circular motions, up and down motions, or zigzag motions (the motions being insufficient to cause debridement and abrasion of the affected skin) on the moistened areas for about 15 to about 30 seconds. A thin film of wetted sodium chloride results. The subject allows the film to remain and to dry.

The once or twice daily application continues for 2 to 15 weeks. Depending on the mildness to severity of the condition and/or the particular condition, generally at some point between 2 weeks and 5 weeks, the condition begins to be alleviated, and is usually eliminated within another 2 to 3 weeks. Most subjects continue with the once or twice per day application of NaCl to maintain the clarity from the condition.

Specifics for each of the fifteen test subjects are as follows:

Test Subjects Nos. 1, 2, and 3. These persons are young adult females each of whom is afflicted with moderate eczema. In the past, each subject has tried various oral antibiotics, as well as topical antibiotics, with poor results.

At the time of testing with the spool, each subject does not take any medication orally and does not use any medication topically. Each subject starts daily application with the NaCl spool that continues for 10 weeks, and reports having significant improvement as compared to other medications previously used. Each subject has less infection and a quicker healing after the use of the spool. Also, subject no. 3 reports that she has less reddish skin area and rates the intensity of redness as noticeably less redness. The three subjects continue once or twice per day application of NaCl.

Test Subjects No. 4 and 5. These persons are a young adult male with moderate psoriasis and a young adult male with slight psoriasis. In the past, each subject has tried various oral antibiotics, as well as topical antibiotics, with poor results.

At the time of testing with the NaCl spool, each subject does not take any medication orally and does not use any medication topically. Each subject starts daily application with the spool that continues for 10 weeks, and reports having significant improvement as compared to other medications previously used. Also, each subject has less infection and a quicker healing after the use of the spool. The two subjects continue once or twice per day application of NaCl.

Test Subjects Nos. 6 and 7. These persons are two adult males each of whom is afflicted with warts on one hand. The procedure for male subject no. 1 in Example I, except with the NaCl spool, is repeated and substantially similar results are obtained.

Test Subject No. 8. This person is a middle-aged adult male with dermatosis. He reports that when his work is stressful, he notices flare-ups for long periods of time. In the past, he has been to dermatologists and tried various oral antibiotics, as well as topical antibiotics. With use daily of the NaCl spool applied to the affected areas of his skin, he reports having significant improvement as compared to other medications previously used. Also, he reports that he has less reddish skin area and rates the intensity of redness as significantly less redness.

Test Subject No. 9. This person is a middle-aged adult male who is subject to repeated bouts of impetigo. During a bout, he reports having significant improvement with daily application of the NaCl spool to the affected areas of his skin as compared to other medications previously used for previous bouts. Also, he reports that he has less reddish skin area and rates the intensity of redness as significantly less redness.

Test Subject No. 10. This person is a male senior citizen with neurodermatitis. He reports that he has improvement while using the NaCl spool in daily application to the affected areas of his skin. He has less infection and a quicker healing after the use of the NaCl spool.

Test Subject No. 11. This person is a female senior citizen with pruritis. With daily application of the NaCl spool to the affected areas of her skin, she reports having a little improvement as compared to other medications previously used for topical treatment of her pruritis. Also, she reports that she has less reddish skin area and rates the intensity of redness as slightly less redness. However, it is believed that she does not achieve better results because she also indicates that she forgets to be consistent in daily use.

Test Subject No. 12. This person is a female senior citizen with erythema. She reports having slight improvement from daily application of the NaCl block to the affected areas of her skin as compared to other medications previously used for topical treatment of her erythema. She has less infection and a quicker healing of after the use of the NaCl spool. Also, she reports that sometimes she has less reddish skin area and rates the intensity of redness as slightly less redness.

Test Subject Nos. 13 and 14. One person is a female infant about 6 months old and one person is an incontinent female senior citizen in a nursing home. Each has diaper rash. After thorough washing of the buttocks area of each with soap and water to ensure urine and fecal matter are removed, each buttocks area is left wet after rinsing with water. Then, the NaCl spool is applied once daily to the buttocks area of each female. After 3 days, the diaper rash of each female is alleviated.

Test Subject No. 15. This person is a young adult male with jock itch. After washing during his morning shower, he towels dry, except for his genital area. Then, he applies the NaCl to his genital area once daily. After 3 days, his jock itch is alleviated.

It will be understood that various details of the invention may be changed without further departing from the scope of the invention. Furthermore, the foregoing description is for the purpose of illustration only, and not for the purpose of limitation—the invention being defined by the claims.

What is claimed is:

1. A method for achieving improvement in a dermatological condition by the topical treatment of human skin affected with the dermatological condition, wherein the dermatological condition is selected from the group consisting of impetigo, epidermolysis bullosa, eczema, neurodermatitis, psoriasis, pruritis, erythema, hidradenitis suppurativa, warts, diaper rash, jock itch, and combinations thereof, said method comprising of the steps of:

(a) applying a composition consisting essentially of sodium chloride on the affected skin in a manner insufficient to cause abrasion and debridement of the affected skin;

(b) allowing the applied sodium chloride to remain on the affected skin; and (c) wherein steps (a) and (b) are accomplished at least once per day.

2. The method of claim 1, wherein the applied sodium chloride in step (b) forms a film on the affected skin.

3. The method of claim 1, wherein the sodium chloride is in a form selected from the group consisting of a solid block of substantially pure sodium chloride and an aqueous solution containing at least about 5% by weight of sodium chloride.

4. The method of claim 3, wherein the solid block of sodium chloride is about 95% to about 100% by weight sodium chloride.

5. The method of claim 3, wherein the solid block of sodium chloride is free of having a carrier incorporated therewith.

6. The method of claim 3, wherein applying the solid block of sodium chloride in step (a) is accomplished by gently gliding the solid block of sodium chloride over the affected skin.

7. The method of claim 6, wherein gliding the solid block of sodium chloride over the affected skin is accomplished in a time ranging from about 60 seconds to about 1 second.

8. The method of claim 6, wherein prior to gliding the solid block of sodium chloride over the affected skin, the affected skin is pre-moistened with water, and then gliding the solid block of sodium chloride over the affected skin results in the sodium chloride becoming wet, and then in step (b), the wetted applied sodium chloride remaining on the affected skin is allowed to dry on the affected skin.

* * * * *